US011998343B2

(12) United States Patent
Bar-on et al.

(10) Patent No.: US 11,998,343 B2
(45) Date of Patent: Jun. 4, 2024

(54) ANNOTATION OF SLOW ELECTROPHYSIOLOGICAL (EP) CARDIAC PATHS RELATED TO VENTRICULAR TACHYCARDIA (VT)

(71) Applicant: BIOSENSE WEBSTER (ISRAEL) LTD., Yokneam (IL)

(72) Inventors: Tal Haim Bar-on, Kiryat Tivon (IL); Meir Bar-Tal, Haifa (IL); Gal Hayam, Tivon (IL); Einat Shapira, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 167 days.

(21) Appl. No.: 17/234,032

(22) Filed: Apr. 19, 2021

(65) Prior Publication Data
US 2022/0330877 A1 Oct. 20, 2022

(51) Int. Cl.
*A61B 5/363* (2021.01)
*A61B 5/00* (2006.01)
(Continued)

(52) U.S. Cl.
CPC .............. *A61B 5/363* (2021.01); *A61B 5/287* (2021.01); *A61B 5/308* (2021.01); *A61B 5/333* (2021.01);
(Continued)

(58) Field of Classification Search
CPC ......... A61B 5/343; A61B 5/363; A61B 5/367; A61B 5/339; A61B 2018/00839
See application file for complete search history.

(56) References Cited

U.S. PATENT DOCUMENTS

| 9,662,178 B2 | 5/2017 | Nanthakumar |
| 2016/0128785 A1* | 5/2016 | Nanthakumar ........ A61B 5/366 600/374 |

(Continued)

FOREIGN PATENT DOCUMENTS

| WO | WO2014183206 A1 | 11/2014 |
| WO | WO2018073722 A1 | 4/2018 |

OTHER PUBLICATIONS

European Search report for corresponding EPA No. 22168800.5 dated Sep. 23, 2022.
(Continued)

*Primary Examiner* — George R Evanisko
(74) *Attorney, Agent, or Firm* — Dergosits & Noah LLP; Todd A. Noah

(57) ABSTRACT

A method for evaluation of electrical propagation in the heart includes receiving a pacing signal applied to a heart of a patient, the pacing signal including a sequence of normal and shorter, abnormal, pacing stimuli. A responsive cardiac signal is received, that is sensed by electrodes at a location in the heart and on the body surface of the patient. A model response is found and annotated from evoked potentials caused by the normal pacing stimuli. A correlation is made between the model response along the different signal sections to find and calculate a normal and decremental time delays between the pacing stimuli and respectively resulting evoked potentials at a tissue location. A time difference is calculated, between the normal time delay and the decremental time delay. An EP map of at least a portion of the heart is presented to a user, with a graphical indication of the time difference presented at the tissue location.

22 Claims, 4 Drawing Sheets

(51) Int. Cl.
    *A61B 5/287*     (2021.01)
    *A61B 5/308*     (2021.01)
    *A61B 5/333*     (2021.01)
    *A61B 5/343*     (2021.01)

(52) U.S. Cl.
    CPC .............. *A61B 5/343* (2021.01); *A61B 5/743* (2013.01); *A61B 2562/04* (2013.01)

(56) References Cited

U.S. PATENT DOCUMENTS

2018/0089825 A1    3/2018   De Chillou
2019/0298213 A1   10/2019   Niederer

OTHER PUBLICATIONS

Jackson Nicholas et al: "Decrement Evoked Potential Mapping: Basis of a Mechanistic Strategy for Ventricular Tachycardia Ablation", Circulation: Arrhythmia and Electrophysiology, vol. 8, No. 6, Dec. 1, 2015 (Dec. 1, 2015), pp. 1433-1442, XP055958657.

Kautzner et al., "Mapping and Ablation of Unmappable Ventricular Tachycardia, Ventriculr Tachycardia Storm, and Those in Acute Myocardial Infarction," Cardiac Electrophysiology Clinics, 11:4, Nov. 6, 2019, Amsterdam, NL.

* cited by examiner

ANNOTATION OF SLOW ELECTROPHYSIOLOGICAL (EP) CARDIAC PATHS RELATED TO VENTRICULAR TACHYCARDIA (VT)

FIELD OF THE INVENTION

This invention relates generally to electrophysiological (EP) signals, and specifically to a method for evaluation of electrical propagation in the heart.

BACKGROUND OF THE INVENTION

Annotation of electrophysiological signals to determine local activation times (LATs) was previously suggested in the patent literature. For example, U.S. Pat. No. 9,662,178 describes various embodiments for a system and a method for identifying the arrhythmogenic circuit of a patient. In one embodiment, the method comprises obtaining data for electrograms recorded at various locations of the heart while programmed ventricular pacing with extra stimuli was performed, obtaining decrement values for at least two different locations of the heart using the recorded electrograms, generating at least a portion of a decrement map using the decrement values, and identifying the arrhythmogenic circuit based on electrograms having significant decremental properties.

As another example, U.S. Patent Application Publication No. 2018/0089825 describes a method for identifying an isthmus in a three-dimensional map of a cardiac cavity by means of a processing unit configured to perform the following steps: a) correlation between a set of stimulated points of the cardiac cavity, each stimulated point being represented by a set of signals that are obtained following surface electrocardiography (ECG), excluding ventricular tachycardia; b) identification of a watershed line on the basis of the above correlation results and of the 3D coordinates of the stimulated points in the 3D map; and c) determination of the isthmus based on a 3D corridor substantially transverse to the watershed line.

PCT International Publication WO 2018/073722 describes a computer implemented method to identify the ventricular arrhythmogenic substrate in myocardial scar or fibrotic tissue and computer program products. A plurality of mapping points acquired from a patient are stored in a signal acquisition unit, the mapping points including ECG signals, electrogram (EGM) signals and a 3D location of the EGM signals, the method comprising for a reference mapping point: a) detecting each beat present in one recorded ECG signal and identifying a beat of interest from the detected beats; b) identifying a principal EGM wave related to the identified beat of interest; c) identifying an onset and an end time landmarks of said principal EGM wave providing a primary delineated EGM signal and measuring a voltage amplitude of the primary delineated EGM signal; d) performing a further analysis of the primary delineated EGM; and e) creating a conducting channel map and a propagation map of the heart based on the result of a tagging performed during the analysis.

SUMMARY OF THE INVENTION

An embodiment of the present invention provides a method including receiving a pacing signal applied to a heart of a patient, the pacing signal including (i) a sequence of normal pacing stimuli at sinus-rate intervals, and (ii) one or more abnormal pacing stimuli at abnormal intervals that are shorter than the sinus-rate intervals. A cardiac signal is received, that is sensed in response to the pacing signal, by electrodes at a location in the heart and on the body surface of the patient. A model response is found and annotated from evoked potentials caused by the normal pacing stimuli. A correlation is made between the model response along the different signal sections to find the annotations of the first evoked potentials caused by the normal pacing stimuli, as well as of the second evoked potentials caused by one or more abnormal pacing stimuli, according to index in the signal section that received the highest scoring with the model response. The first and second time delays are calculated. A time difference is calculated, between the normal time delay and the decremental time delay. An EP map of at least a portion of the heart is presented to a user, with a graphical indication of the time difference presented at the tissue location.

In some embodiments, correlating with model response includes weighting the correlation depending on a derivative of the one or more signals.

In some embodiments, estimating the first time delay and the second time delay includes annotating the bipolar signal at the estimated first and second delays.

In an embodiment, the method further includes receiving a respective electrocardiogram (ECG) signal from electrodes external to the patient and, using the ECG signal, estimating whether a stable contraction occurred in response to the a predefined number of normal pacing stimuli and to the first abnormal pacing stimuli. A portion of the cardiac signal for which the respective ECG does not indicate stable contraction is discarded.

In some embodiments, estimating the stable contraction includes estimating a repeatability of evoked potentials in the bipolar signal. In other embodiments, estimating the stable contraction includes smoothing the bipolar signal and detecting the evoked potentials in the smoothed bipolar signal.

In an embodiment, estimating one or more correlations includes identifying far field from near field signals.

In some embodiments, presenting the EP map includes adjusting a scale of a GUI to define a minimal positive value of the time difference to be displayed on the EP map.

In other embodiments, presenting the EP map includes overlaying on the EP map an artificial icon, which is graphically coded to indicate a value of the time difference.

In yet other embodiments, presenting the EP map further includes indicating to the user an occurrence of aberrant ventricular activity.

In an embodiment, indicating the occurrence of aberrant ventricular activity includes using at least one of a color and surface morphology on the EP map.

In an embodiment, receiving the cardiac signal includes receiving unipolar and bipolar electrograms acquired using a catheter.

In some embodiments, estimating a highest scoring correlation includes training a machine learning model to estimate a highest scoring correlation based on a prespecified metric.

There is additionally provided, in accordance with another embodiment of the present invention, a system, including an interface and a processor. The interface is configured to receive a pacing signal applied to a heart of a patient, the pacing signal including (i) a sequence of normal pacing stimuli at sinus-rate intervals, and (ii) one or more abnormal pacing stimuli at abnormal intervals that are shorter than the sinus-rate intervals. The interface is further configured to receive a cardiac signal that is sensed, in response to the pacing signal, by electrodes at a location in the heart and on the body surface of the patient. The processor is configured to (a) find and annotate a model response from the evoked potentials caused by the normal pacing stimuli, (b) correlate between the model response along the different signal sections to find the annotations of the first evoked potentials caused by the normal pacing stimuli, as well as of the second evoked potentials caused by one or more abnormal pacing stimuli, according to index in the signal section that received the highest scoring with the model response, (c) calculate the first and second time delays, (d) calculate a time difference between the normal time delay and the decremental time delay, and (e) present an EP map of at least a portion of the heart to a user, with a graphical indication of the time difference presented at the tissue location.

BRIEF DESCRIPTION OF THE DRAWINGS

The present disclosure will be more fully understood from the following detailed description of the embodiments thereof, taken together with the drawings, in which.

DETAILED DESCRIPTION OF EMBODIMENTS

Overview

Figure 1:
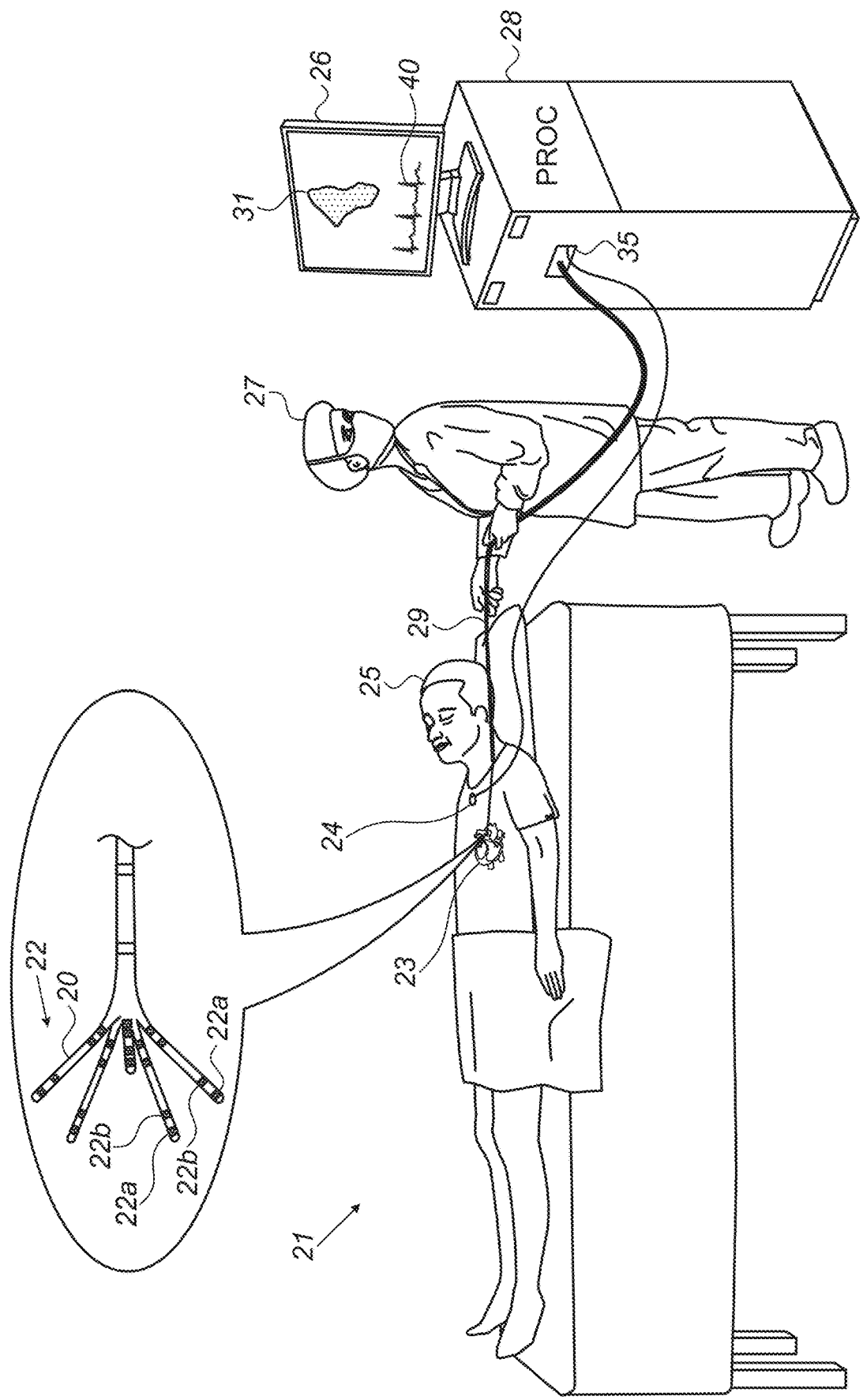
FIG. 1 is a schematic, pictorial illustration of a catheter-based electrophysiological (EP) mapping system in accordance with an exemplary embodiment of the present invention.

Cardiac tachycardia, such as ventricular tachycardia (VT) or atrial tachycardia, is a heart rhythm disorder (arrhythmia) caused by abnormal electrical signals in a heart chamber. For example, VT may be caused by abnormal electrical signals in the lower chambers of the heart (ventricles). VT may be caused by local electrophysiological (EP) conduction defects in ventricle tissue, such as in scar tissue. To find and treat such arrhythmogenic locations, for example by ablation, the ventricle may be paced and EP mapped using catheters to identify aberrant tissue locations (e.g., locations demonstrating delayed evoked potentials) that may be causing the VT.

In particular, EP mapping may be done in support of a treatment approach, called "scar-homogenization," which has been found useful to ablate scar tissue over an entire area of the scar. The motivation behind the ablative treatment is to target poorly coupled ventricle tissue fibers surviving within a developed scar. These bundles are deemed to generate EP paths exhibiting slow conduction (scar isthmuses) believed to be responsible for VT. To this end, EP mapping of scar tissue, followed by scar homogenization, appears thus far to be an optimal procedural endpoint to eliminate VT.

In order to perform EP mapping of the pathways and circuits that lead to the tachycardia, usually the tachycardia will be initiated during the EP study. However, as VT is often non-inducible or hemodynamically unstable, substrate mapping is often necessary. In substrate mapping, characteristics of the tissue in sinus rhythm or ventricular pacing are being related to the arrhythmogenicity of the tissue.

Embodiments of the present invention that are described hereinafter provide methods and systems that automatically identify and analyze delayed evoked potentials while only using substrate mapping for pacing a cardiac chamber, such as a ventricle. In the disclosed embodiments, an automated decrement-evoked potential (DeEP) detection method is used in order to automatically detect, analyze, annotate, calculate and present abnormally delayed evoked potentials in electrograms (e.g., bipolar electrograms), which are indicative of scar isthmuses.

DeEP mapping is a substrate mapping technique. The basis for this method is that ventricular tissue that displays decremental conduction with a decremental extra-stimulus, appears to be more specific to the aberrant VT circuits. The DeEP information is typically presented as a DeEP data layer overlaid on an EP map of the ventricle.

In the disclosed technique, the ventricle is paced with short sequences of normal sinus-rate pulses. The short sequences end with one or more pulses (typically three at most) having shorter inter-pulse intervals. Common notation defines this as pacing with a train of S1 paces (usually, but not always, having cycle length of 600 ms) followed by one or more decremental extra-stimuli (S2, S3, etc.) delivered shortly after (e.g., 20 milliseconds after) a period of time (commonly referred to as the refractory period) that a new action potential cannot normally be initiated, so as to stimulate the looked for arrhythmogenic response in aberrant tissue.

In the context of this description the wording "normal sinus-rate pulses" covers pulses that are equidistant up to a predefined variation. For example, a sequence of pulses with an interval 600±6 milliseconds are included in the definition. More generally, a sequence of pulses with any given equidistant interval (e.g., smaller or larger than 600 milliseconds, such as 500 mSec or 700 mSec) up to the predefined variation are considered hereinafter "normal sinus-rate pulses". Typically, the predefined variation is limited to an order of 1% of the specified equidistant interval. The respective decremental extra-stimuli are defined with respect to the above equidistant interval.

The above described sequence simulates an early beat (premature ventricle contraction, PVC), for invoking delayed potentials in an arrhythmogenic tissue. In response to the normal sinus rate pacing pulses, evoked potentials occur one each with a normal time delay after the stimulus. This normal delay, between a pacing pulse and the resulting evoked potential, is called hereinafter "first time delay." This portion of the EP mapping method is sufficient for characterizing normal tissue.

The short sequences end with one or more short-interval (i.e., decremental) pacing stimuli. For example, if the sinus rate pacing is done with a period of 0.6 sec, the one or more short-interval pacing stimuli are applied at 0.4 sec intervals following the sinus rate stimulus. The terms "pulses" and "stimuli" are used interchangeably herein.

In response to the decremental extra-stimuli, the evoked potential may be delayed (relatively to the first time delay). The areas where there is a meaningful relative delay (e.g., more than 10 mSec) are considered to be more specific to the an aberrant VT circuit. In general, early beat (premature ventricle contraction, PVC) is something relatively common. Only if the early beat encounters an arrhythmogenic tissue, like a tissue that shows slower conduction as a result of the early beat, an aberrant VT circuit can be initiated and maintained. The larger delay than the first time delay, if occurring, of these evoked potentials, relative to the corresponding extra-stimuli pacing pulses, is called hereinafter "second time delay."

A processor analyzes resulting signals, such as bipolar signals acquired by a mapping catheter, which are acquired over time at various tissue locations on the heart surface, and detects the delayed evoked potentials that occur as a result of the one or more short-interval pacing pulses. The processor annotates evoked potentials having the first and second time delays, and calculates a time difference between the second and first time delays, this time difference called hereinafter "DeEP interval."

In some embodiments, the processor performs the following steps at each mapped tissue location to estimate the first and second time delays:
1. Generates one or more decremental (i.e., extra stimuli) paces that potentially cause delayed evoked potential.
2. Determines, for each evoked potential, a candidate annotation during time of the delayed evoked potential. For example, the annotated candidate time may be the center of the short signal section.
   In an exemplary embodiment, annotation of each evoked potential should be in a similar morphological position (e.g., on the same deflection of the response) to maximize reliability of a calculation of DeEPs. In one embodiment, a disclosed annotation process comprises three steps: (i) extraction of a model response out of the responses to S1 paces, which is an evoked potential with high correlation to the other S1-pace evoked potentials in the EGM, and specifically to the last 3-4 responses post an S1 pace, (ii) annotation of the model response, e.g., in the center of mass, or, preferably, in the last deflection of the response, and (iii) annotation of the other evoked potentials, including responses to the extra stimuli, based on a scoring computed with the model response. In an exemplary embodiment, the processor calculates scorings along each signal section of the paced signal (interval between paces, or between the last pace and 350-400 ms after) based on a derivative-weighted-correlation of each section with the model response. In each signal section, the point (e.g., index) that received the highest scoring is chosen as the annotation of that interval.
   After annotating all intervals in the EGM, the algorithm deletes annotations that their scoring is below a pre-defined threshold (low morphological compatibility to the model response). In addition, the disclosed automatic algorithm checks for stability of 3 last post-S1 evoked potentials, by calculating the standard deviation of timing of response (distance of annotation from pace).
3. Calculates the first and second delays using the distance between the chosen annotation of each interval and a relative position. The simplest relative position would be the pace before each response. In another embodiment, while the annotation is considered as the marking of the local near field response, the relative position could be a marking of the far field response (then, the distance is measured between the near field and far field responses after the pace).

More generally, the processor can estimate a degree of correlation by any other methods known in the art, such as by using machine learning, and define a scoring, to find a correlation with a highest scoring. For example, the scoring may be based on a prespecified metric, such as L1.

In an exemplary embodiment, values of the DeEP interval (i.e., time differences) are graphically coded (e.g., longer DeEP intervals are marked by larger tags (e.g., sphere-icons).

In an exemplary embodiment, a GUI is provided to assist a physician to determine to what extent a given DeEP interval is indicative of a location of a scar isthmus causing VT. The GUI includes an adjustable scale that the physician can use to show only DeEPs longer than a (positive) threshold value on the map.

Typically, the processor is programmed in software containing a particular algorithm that enables the processor to conduct each of the processor-related steps and functions outlined above.

By applying automated DeEP annotation algorithm to map local cardiac (e.g., ventricle) tissue locations inducing VT, the disclosed invasive cardiac diagnostic method may improve the safety and value of diagnostic catheterization procedures.

System Description

FIG. 1 is a schematic, pictorial illustration of a catheter-based electrophysiological (EP) mapping system 21, in accordance with an exemplary embodiment of the present invention. FIG. 1 depicts a physician 27 using an electro-anatomical mapping catheter 29 to perform an electro-anatomical mapping of a heart 23 of a patient 25. Mapping catheter 29 comprises, at its distal end, one or more arms 20, each of which is coupled to a bipolar electrode 22 comprising adjacent electrodes 22a and 22b.

During the mapping procedure, the locations of electrodes 22 are tracked while they are inside heart 23 of the patient. For that purpose, electrical signals are passed between electrodes 22 and external electrodes 24. For example, three external electrodes 24 may be coupled to the patient's chest, and another three external electrodes may be coupled to the patient's back. (For ease of illustration, only one external electrode is shown in FIG. 1.)

Based on the signals, and given the known positions of electrodes 24 on the patient's body, processor 28 calculates an estimated location of each electrode 22 within the patient's heart. Respective electrophysiological data, such as bipolar electrogram traces, are additionally acquired from tissue of heart 23 by using electrodes 22. The processor may thus associate any given signal received from electrodes 22, such as a bipolar EP signal, with the location at which the signal was acquired. The processor 28 receives the resulting signals via an electrical interface 35, and uses information contained in these signals to construct an electrophysiological map 31 and ECG traces 40, and to present these on a display 26.

Processor 28 typically comprises a general-purpose computer with software programmed to carry out the functions described herein. The software may be downloaded to the computer in electronic form, over a network, for example, or it may, alternatively or additionally, be provided and/or stored on non-transitory tangible media, such as magnetic, optical, or electronic memory. In particular, processor 28 runs a dedicated algorithm as disclosed herein, including in FIG. 4, that enables processor 28 to perform the disclosed steps, as further described below.

The example illustration shown in FIG. 1 is chosen purely for the sake of conceptual clarity. Other types of electrophysiological sensing catheter geometries, such as the Lasso® Catheter (produced by Biosense-Webster Inc., Irvine, California) may be employed. Additionally, contact sensors may be fitted at the distal end of mapping catheter 29 to transmit data indicative of the physical quality of electrode contact with tissue. In an exemplary embodiment, measurements of one or more electrodes 22 may be discarded if their physical contact quality is indicated as poor, and the measurements of other electrodes may be regarded as valid if their contact quality is indicated as sufficient.

Annotation of Slow Ep Cardiac Paths Related to VT

Figure 2:
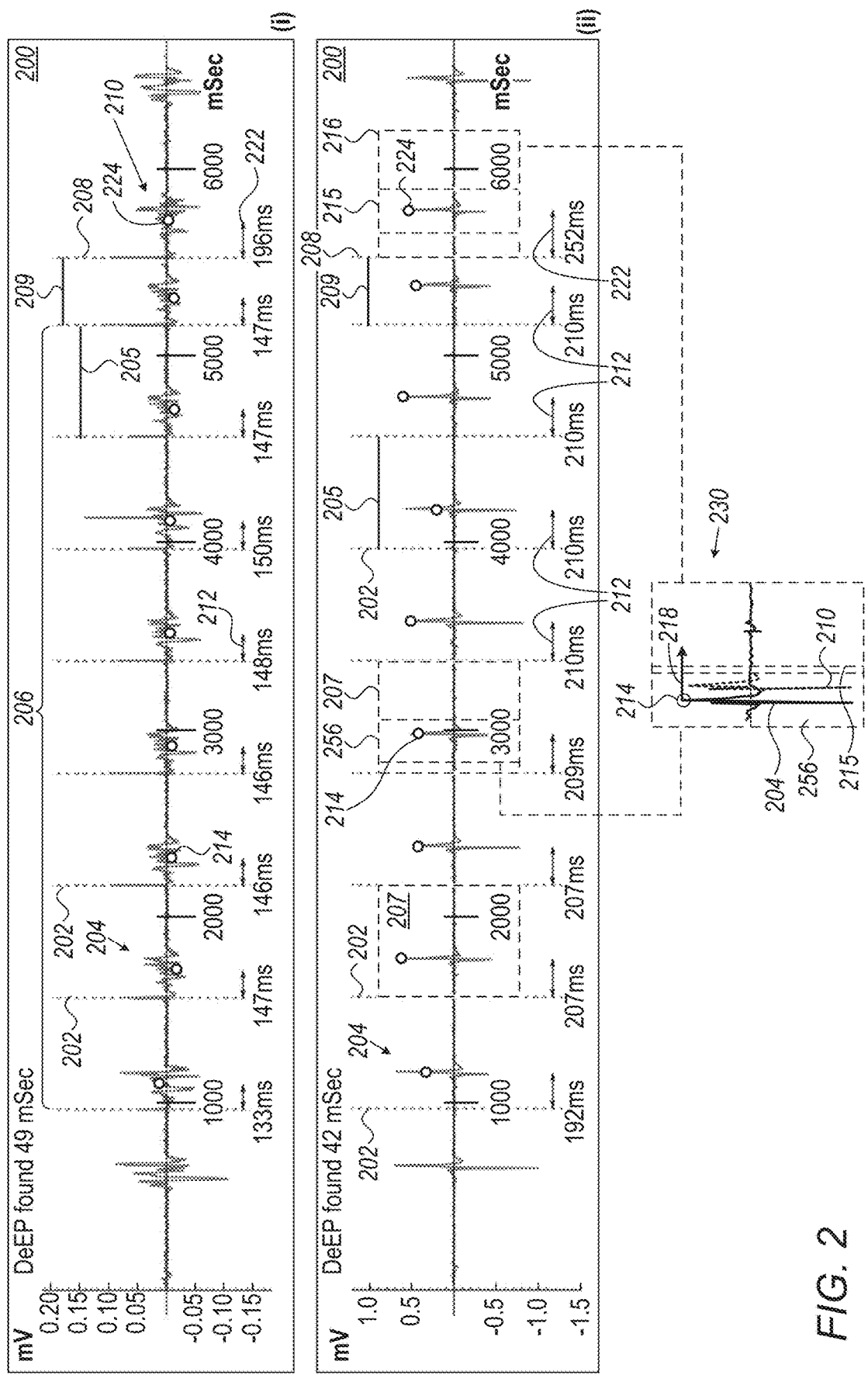
FIG. 2 shows example graphs of bipolar electrograms acquired using the system of FIG. 1, with decrement-evoked potentials (DeEPs) annotated on the bipolar signals, according to an exemplary embodiment of the present invention.

FIG. 2 shows example graphs of bipolar electrograms 200 acquired using system 21 of FIG. 1, with decrement-evoked potentials (DeEPs) annotated (224) on the bipolar signals, according to an exemplary embodiment of the present invention. Graphs (i) and (ii) each show a short sinus rate pacing stimuli section 207 within an entire s1-paced section 206 comprising a sequence of normal equidistant (205) pacing stimuli 202, and resulting evoked potentials 204. One of sections 207 is found to include the aforementioned model response 256 having an annotation 214. Model response 256 is chosen because its entire 207 section have the highest correlation to the other 207 sections. In an embodiment, a processor cuts model response 256 out of its section 207 according to a time duration of about 170-200 msec, starting about 70 msec after the pace 202. In another embodiment, this is performed by the processor annotating the interval (the interval 205 of section 207 that holds the response 256) by using another annotation algorithm (e.g., an algorithm made by Biosense Webster to identify local activity in intracardiac signals), and searching for the "quiet zones" around the annotation (where the response starts and ends).

The last pacing stimulus 208 is decremental, as it is applied after a shorter time interval 209 than of the normal sinus rate, which may induce a delayed evoked potential 210. In graphs (i) and (ii), interval 205 is 0.6 seconds and short-interval 209 is only 0.35 seconds.

The brief sequence of the normal sinus rate pacing stimuli 202 (in graphs (i) and (ii), section 206 includes seven periods), which typically results in a stable cardiac response, with almost equal time delays 212 between each of S1 pacing stimuli 202 and the resulting annotated (214) evoked potentials 204. As a result, a well-defined "first time delay" can be derived, for example using the last time delay 212 or by averaging the latest five delays 212 (before pacing stimulus 208). In graphs (i) and (ii) the first time delays are 147 mSec and 210 mSec, respectively.

In an embodiment, a disclosed algorithm includes checking for stability of three last post-S1 evoked potentials 204, by calculating the standard deviation of timing of response (i.e., of delay 212 of annotation from pace). If the standard deviation is below a given threshold, the timing of response is considered well defined and useful, and the processor selects an average of the three or the latest as the delay 212 to use in a subsequent calculation of a DeEP.

As noted above, short-interval stimulus 208 may produce a different cardiac response, e.g., of an evoked potential with a "second time delay" 222 indicative of abnormal tissue. This is seen in a block 216 including a portion 215 of the S2 evoked potential (with an annotation 224 that is derived as described below)

To find annotations 214 and 224, processor 28 performs the following scanning correlation process:

In each section 207, 209 or between the last 208 pace and 350-400 ms after (216), the processor correlates each S1 block (with its evoked potential 204) with the extracted model response for this 200 block. The scanning starts for each section 207/209/216, with the annotation index of the model response 214 (chosen as the center of mass of the 256, or, preferably, at the last deflection) aligned to the beginning of the section, and moving the aligning index by index "i" of Eq. 1 below—and in each such index i of the time axis of the block calculating the result using Eq. 1. A typical time step between consecutive indices is 1 msec.

The processor choses the index with highest scoring to be the timed annotation of the interval (214 in S1 and 224 in S2) where the processor calculated the highest scoring using Eq. 1.

Annotation point 224 is also estimated using the disclosed derivative-weighted-correlation annotation scoring method. As seen in inset 230, model response 256 is correlated with S2 signal section 215, and an index having the highest scoring is selected by processor 28 as annotation 224. The correlation process between model response 256 and decremental signal section 215 is illustrated in inset 230 using a dotted arrow 218.

As can be seen in graphs (i) and (ii), evoked potentials may be characterized by strong deflections (large derivatives) of the signal. In an embodiment, the correlation is weighed by the magnitude of the derivative to enhance a scoring accuracy.

During the derivative-weighted-correlation step, also called herein "scanning," processor 28 computes the scoring, which is a combination of correlation with favorability to a high derivative, i.e., at each point of the scan, processor 28 calculates:

$$\text{Score}(t_j) = C \cdot \sum_{i=1}^{n} v_i \cdot u_i(t_j) \cdot |u'_i(t_j)| \quad \text{Eq. 1}$$

where $v_i$ refers to a bipolar point in either a sinus-rhythm section 207 or decremental section of the bipolar signal, $u_i$ refers to a point in section 256, $|u'_i|$ is its derivative magnitude at this point, n is the length of section 215 (in msec), and $t_j$ is a candidate time for annotation in section 215. $t_j$ is an annotation point of a section 215 for which the scoring is calculated, using Eq. 1, of which one highest scoring point of a set $\{t_j\}$ is chosen as the point to annotate (224) delayed-evoked potentials 204 and 210.

In some embodiments, the processor uses Eq. 1 of the algorithm (or a similar equation) to check a degree of correlation of sinus rate bipolar signal sections 207 one with the other, and using the correlation procedure, selects an annotation 214 among the S1 blocks that yield the highest scoring to receive model response 256.

Processor 28 then selects an annotation point 224 that has the highest derivative-weighted-correlation scoring among candidate annotations points 220 of the defined sections 215.

Once the VT-suspected evoked potential is annotated (224), a delay time 222 can be calculated. The DeEP interval is defined as the time difference between delays two and one at the tissue location:

$$\text{DeEP interval}=[\text{delay 222}]-[\text{delay 212}] \quad \text{Eq. 2}$$

Typically, to be clinically significant, the time difference should be well above several mSec. Shown time differences (i.e., DeEP intervals) 222 in FIG. 2 of more than 40 mSec are strong indications of a tissue location causing VT. A physician can adjust a GUI to show only what are considered clinically "significant" DeEP intervals, by adjusting a DeEp threshold (always a positive value), as shown in FIG. 3.

Eq. 1 is brought by way of example. Other scoring equations may also be used to provide the required selection of best annotations.

Figure 3:
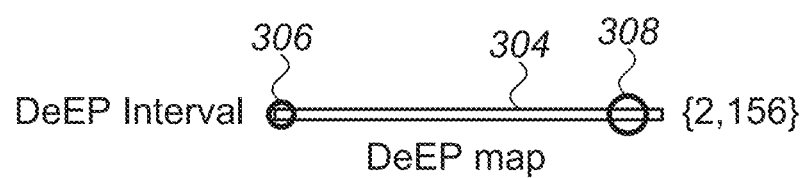
FIG. 3 is a schematic, pictorial volume rendering of an EP map of a ventricle indicating tissue locations and magnitude of DeEPs that may cause ventricle tachycardia (VT) according to an exemplary embodiment of the present invention.
Figure 3:
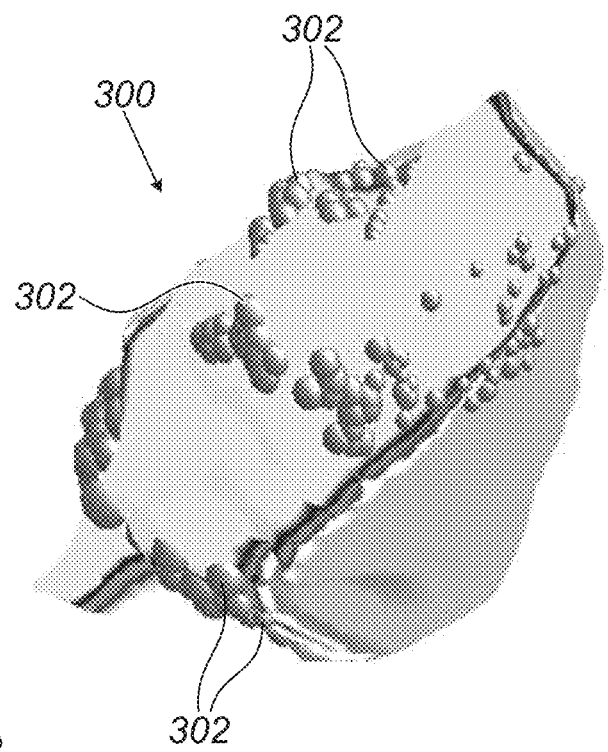

FIG. 3 is a schematic, pictorial volume rendering of electrophysiological (EP) map 300 of a ventricle indicating tissue locations and magnitudes of DeEPs that may cause ventricle tachycardia (VT), according to an embodiment of the present invention.

In the illustrated example, EP map 300 is a voltage map overlaid with ball icons 302 to indicate cardiac tissue locations exhibiting DeEP intervals indicative of VT.

In FIG. 3, a potential risk of VT from a tissue location is defined as a value of a DeEP interval at the location. As seen, cardiac tissue locations exhibiting larger DeEP intervals are marked by larger tags (e.g., ball icons) 302.

As noted above, a physician can adjust a scale 304 of the GUI to show only DeEP intervals above a user-specified positive valued threshold 306. Optionally, the user can set a maximal DeEP interval value 308.

Based on the layer of information of DeEP intervals, a physician, such as physician 27, can plan and perform a careful, selective ablation, with minimal hazard to the patient.

Method of Automatic Detection of DeEP

Figure 4:
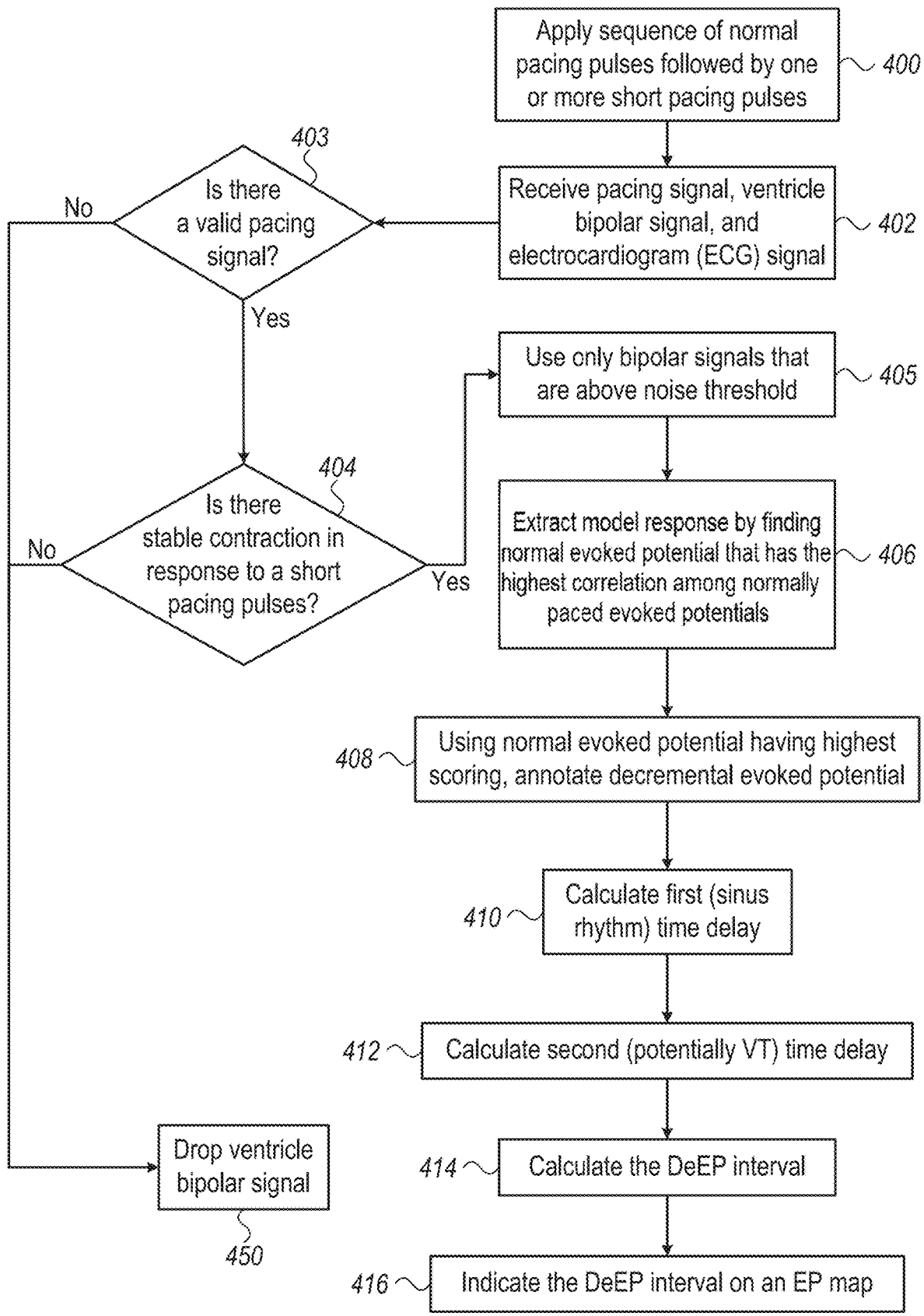
FIG. 4 is a flow chart that schematically illustrates a method and algorithm for the annotation of a DeEP in a bipolar electrogram according to an exemplary embodiment of the present invention.

FIG. 4 is a flow chart that schematically illustrates a method and algorithm for the annotation (S1—214, and S2—224) of a DeEP 210 in a bipolar electrograms 200, according to an exemplary embodiment of the present invention. The algorithm, according to the presented embodiment, carries out a process that begins with system 21 applying a pacing signal is a form of a sequence of normal pacing pulses followed by one or more short pacing pulses, at a pacing step 400.

At EP data receiving step 402, processor 28 receives the pacing signal, the bipolar signal (e.g., waveform) from catheter 29, and respective ECG signal from a body surface (BS) electrode. First the processor checks if there is a valid s1 and s2 pacing signal, at a pacing verification step 403. If not, the processor drops the batch of signals, at a signal dropping step 450.

Next, at stable contraction validation step 404, processor 28 estimates from the body-surface ECG signal if stable cardiac muscle contractions occurred in response to the sinus rate pacing and to the extra stimulus pacing. If not, the processor the batch of signals, at a signal dropping step 450. By checking contraction, the processor typically checks that:
1. there is stable contraction of the heart in response to the s1 paces for a predefined number of normal pacing stimuli (typically 3 to 4 such), especially in the last 4 intervals posts of an s1 pacing, and 2. there is response to the first extra stimulus. In an embodiment, estimating the stable contraction comprises estimating a repeatability in time (e.g. stability of time intervals 205) of evoked potentials in the bipolar signal.

At a noise thresholding step 405, the processor checks received bipolar signal blocks amplitudes against a noise threshold. In this step, the processor checks which channels in the bipolar EGM data passed a pre-decided noise threshold. This is done, for example, by checking the maximum amplitude in each interval, such as intervals 205 and 209. However other criteria may be used, such as checking an SNR of the peak amplitude. The minimum threshold value can be selected based on known properties of EGMs, or given as a choice for a user to input. The EGMs that passed noise threshold continue to an annotation step.

Next, a model response extraction step 406, processor finds model response 256, as that of one of evoked potential signals 204 which has the highest correlation among signals 204. The processor annotates model response 256 in the center of mass or by using an annotation algorithm made by Biosense Webster to identify late potentials to choose last deflections (embodiments).

Next, processor 28 correlate model response 256 with the rest of the normal evoked potentials (204) and of decremental signal section 215, and annotates the time index on the signal which has the highest correlation with an annotation 214 or 224 (respectively), at a signal annotation step 408.

Using stimuli 202 timings and annotation 214, processor 28 calculates the first time delay, at a first delay calculation step 410. This first time delay can be calculated as the average of several calculated delays 212.

Using stimulus timing 208 and selected annotation 224, processor 28 calculates second time delay 222, potentially indicative of a tissue location that causes VT, at a second delay calculation 412.

At a DeEP interval calculation step 414, processor 28 calculates, using Eq. 2, the DeEP interval.

Finally, processor 28 indicates the DeEP interval on an EP map, as shown in FIG. 3, at an DeEP interval overlying step 416.

In an embodiment, during steps 406-408 a processor annotates the latest near field response in the segment (e.g., using an annotation algorithm made by Biosense Webster to identify late potentials). In another embodiment the processor identifies the far field response of the segment, for example, by marking the first meaningful deflection in the unipolar intracardiac channels. In that embodiment—the delays will be calculated between the near field response and the far field response (and not of the response form the pace).

The example flow chart shown in FIG. 4 is chosen purely for the sake of conceptual clarity. The present embodiment may also comprise additional steps of the algorithm, such as receiving multiple bipolar signals and ECG signals simultaneously, as well as receiving indications of the degree of physical contact of the electrodes with diagnosed tissue from a contact force sensor. This and other possible steps are omitted from the disclosure herein purposely in order to provide a more simplified flow chart.

Although the embodiments described herein mainly address cardiac diagnostic applications, the methods and systems described herein can also be used in other medical applications.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:
1. A method for evaluation of electrical propagation in a heart of a patient, the method comprising:
applying a pacing signal to the heart of the patient by electrodes on a catheter, the pacing signal comprising
(i) a sequence of normal pacing stimuli at sinus-rate intervals, and (ii) one or more abnormal pacing stimuli at abnormal intervals that are shorter than the sinus-rate intervals;

receiving, in response to the applied pacing signal, a cardiac signal that is sensed by the catheter electrodes at a location in the heart;

identifying and annotating a model response from evoked potentials in the cardiac signal caused by the normal pacing stimuli, the annotated model response being one of the evoked potentials having a high correlation of stimulated points of cardiac activity to the other evoked potentials in the cardiac signal;

determining, for each interval between paces of the paced signal, scorings of correlations with the model response along each of the respective intervals between paces of the paced signal;

annotating a first set of the evoked potentials in the cardiac signal caused by the normal pacing stimuli and a second set of the evoked potentials in the cardiac signal caused by the one or more abnormal pacing stimuli, the first and second sets of evoked potentials being other than the evoked potential of the model and being annotated based upon the scorings of correlations, each annotation in each interval of the paced signal being identified as an index that received the highest scoring with the model response for that interval;

determining a first time delay between the normal pacing stimuli and the resulting evoked potentials in the cardiac signal and a second time delay between the abnormal pacing stimuli and the resulting evoked potentials in the cardiac signal;

determining a decremental time delay, the decremental time delay being a time difference between the first time delay and the second time delay; and presenting an EP map of at least a portion of the heart to a user, with a graphical indication of the decremental time delay presented at the one or more locations in the heart.

2. The method according to claim 1, wherein determining the first time delay and the second time delay comprises annotating the cardiac signal at the determined first and second delays.

3. The method according to claim 1, and comprising receiving a respective electrocardiogram (ECG) signal from electrodes external to the patient and, using the ECG signal, estimating whether a stable contraction occurred in response to a predefined number of normal pacing stimuli and to a first abnormal pacing stimuli, and discarding a portion of the cardiac signal for which the respective ECG does not indicate stable contraction.

4. The method according to claim 3, wherein estimating the stable contraction comprises estimating a repeatability of the evoked potentials in the cardiac signal.

5. The method according to claim 3, wherein estimating the stable contraction comprises smoothing the cardiac signal and detecting the evoked potentials in the smoothed bipolar signal.

6. The method according to claim 1, wherein presenting the EP map comprises adjusting a scale of a GUI to define a minimal positive value of the time difference to be displayed on the EP map.

7. The method according to claim 1, wherein presenting the EP map comprises overlaying on the EP map an artificial icon, which is graphically coded to indicate a value of the time difference.

8. The method according to claim 1, wherein presenting the EP map further comprises indicating to the user an occurrence of aberrant ventricular activity.

9. The method according to claim 8, wherein indicating the occurrence of aberrant ventricular activity comprises using at least one of a color and surface morphology on the EP map.

10. The method according to claim 1, wherein receiving the cardiac signal comprises receiving unipolar and bipolar electrograms from the electrodes.

11. The method according to claim 1, wherein determining the highest scoring correlation comprises training a machine learning model to estimate a highest scoring correlation based on a prespecified metric.

12. A system for evaluation of electrical propagation in a heart of a patient, the system comprising:
    a catheter having a plurality of electrodes configured to apply a pacing signal to the heart of the patient;
    one or more processors; and
    a non-transitory computer readable medium storing a plurality of instructions, which when executed, cause the one or more processors to:
    apply a pacing signal to the heart of the patient by the electrodes on the catheter, the pacing signal comprising (i) a sequence of normal pacing stimuli at sinus-rate intervals, and (ii) one or more abnormal pacing stimuli at abnormal intervals that are shorter than the sinus-rate intervals;
    receive from the catheter electrodes, in response to the applied pacing signal, a cardiac signal that is sensed by the catheter electrodes at a location in the heart; and
    identify and annotate a model response from evoked potentials in the cardiac signal caused by the normal pacing stimuli, the annotated model response being one of the evoked potentials having a high correlation based upon a prespecified metric to the other evoked potentials in the cardiac signal;
    determine, for each interval between paces of the paced signal, scorings of correlations with the model response along each of the respective intervals between paces of the paced signal;
    annotate a first set of the evoked potentials in the cardiac signal caused by the normal pacing stimuli and a second set of the evoked potentials in the cardiac signal caused by the one or more abnormal pacing stimuli, the first and second sets of evoked potentials being other than the evoked potential of the model and being annotated based upon the scorings of correlations, each annotation in each interval of the paced signal being identified as an index that received the highest scoring with the model response for that interval;
    determine a first time delay between the normal pacing stimuli and the resulting evoked potentials in the cardiac signal and a second time delay between the abnormal pacing stimuli and the resulting evoked potentials in the cardiac signal;
    determine a decremental time delay, the decremental time delay being a time difference between the first time delay and the second time delay; and
    cause an EP map of at least a portion of the heart to be presented on a graphical user interface (GUI) electronically coupled to the one or more processors, with a graphical indication of the decremental time delay presented at the one or more locations in the heart.

13. The system according to claim 12, wherein the plurality of instructions further cause the one or more processors to determine the first time delay and the second time delay comprises annotating the cardiac signal at the determined first and second delays.

14. The system according to claim 12, wherein the plurality of instructions further cause the one or more processors to receive a respective electrocardiogram (ECG) signal from electrodes external to the patient and wherein the processor is configured to estimate, using the ECG signal, whether a stable contraction occurred in response to a predefined number of normal pacing stimuli and to the first abnormal pacing stimuli, and to discard a portion of the cardiac signal for which the respective ECG does not indicate stable contraction.

15. The system according to claim 14, wherein the plurality of instructions further cause the one or more processors to estimate the stable contraction by estimating a repeatability of the evoked potentials in the cardiac signal.

16. The system according to claim 14, wherein the plurality of instructions further cause the one or more processors to estimate the stable contraction by smoothing the cardiac signal and detecting the evoked potentials in the smoothed bipolar signal.

17. The system according to claim 12, wherein the plurality of instructions further cause the one or more processors to present the EP map by adjusting a scale of the GUI to define a minimal positive value of the time difference to be displayed on the EP map.

18. The system according to claim 12, the plurality of instructions further cause the one or more processors to cause the EP map to be presented by overlaying on the EP map an artificial icon, which is graphically coded to indicate a value of the time difference.

19. The system according to claim 12, wherein the plurality of instructions further cause the one or more processors to present the EP map by indicating to the user an occurrence of aberrant ventricular activity.

20. The system according to claim 19, wherein the plurality of instructions further cause the one or more processors to indicate the occurrence of aberrant ventricular activity by using at least one of a color and surface morphology on the EP map.

21. The system according to claim 12, wherein the plurality of instructions further cause the one or more processors to receive the cardiac signal by receiving unipolar and bipolar electrograms from the electrodes.

22. The system according to claim 12, further comprising a machine learning model, wherein the plurality of instructions further cause the one or more processors to determine the highest scoring correlation by training the machine learning model to estimate a highest scoring correlation based on a prespecified metric.

* * * * *